United States Patent
Gatzemeyer et al.

(10) Patent No.: US 11,771,214 B2
(45) Date of Patent: Oct. 3, 2023

(54) POWERED ORAL CARE IMPLEMENT INCLUDING A TRACKING MODULE AND TRACKING MODULE THEREOF

(71) Applicant: Colgate-Palmolive Company, New York, NY (US)

(72) Inventors: John Gatzemeyer, Hillsborough, NJ (US); Takahide Okai, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/690,452

(22) Filed: Mar. 9, 2022

(65) Prior Publication Data
US 2022/0192361 A1 Jun. 23, 2022

Related U.S. Application Data

(62) Division of application No. 16/053,840, filed on Aug. 3, 2018, now Pat. No. 11,297,933.

(51) Int. Cl.
*A46B 15/00* (2006.01)
*A61C 17/22* (2006.01)
(Continued)

(52) U.S. Cl.
CPC .......... *A46B 15/0006* (2013.01); *A46B 5/026* (2013.01); *A46B 15/0002* (2013.01);
(Continued)

(58) Field of Classification Search
CPC . A46B 5/026; A46B 15/0002; A46B 15/0006; A46B 15/0038; A46B 15/0097; A61C 17/222; A61C 17/225
See application file for complete search history.

(56) References Cited

U.S. PATENT DOCUMENTS 6,026,532 A * 2/2000 Catanzaro .............. A46B 17/04
132/308
7,600,284 B2 * 10/2009 Hui ...................... A61C 17/225
15/105
(Continued)

FOREIGN PATENT DOCUMENTS

CN 105012035 11/2015
CN 105077973 11/2015
(Continued)

OTHER PUBLICATIONS

International Search Report and Written Opinion of the International Searching Authority in International Application No. PCT/US2019/044780, dated Nov. 4, 2019.

*Primary Examiner* — Randall E Chin

(57) ABSTRACT

An oral care system that includes an oral care implement and a tracking attachment. The oral care implement may include a handle and a head. The tracking attachment is detachably coupled to the oral care implement. The tracking attachment may include a first component comprising a first housing having an inner surface that defines a first cavity and a second component comprising a second housing having an inner surface that defines a second cavity. When the tracking attachment is coupled to the oral care implement, a first portion of the handle is positioned within the first cavity and a second portion of the handle is positioned within the second cavity.

10 Claims, 9 Drawing Sheets

(51) Int. Cl.

| | | |
|---|---|---|
| *A46B 5/02* | (2006.01) | |
| *A46B 17/08* | (2006.01) | |
| *A61C 17/34* | (2006.01) | |
| *A61B 5/00* | (2006.01) | |
| *G16H 40/67* | (2018.01) | |

(52) U.S. Cl.
CPC .......... *A46B 15/0038* (2013.01); *A46B 17/08* (2013.01); *A61B 5/486* (2013.01); *A61C 17/222* (2013.01); *A61C 17/225* (2013.01); *A61C 17/3481* (2013.01); *G16H 40/67* (2018.01); *A46B 2200/1066* (2013.01)

(56) References Cited

U.S. PATENT DOCUMENTS

| | | | |
|---|---|---|---|
| 7,917,986 B2* | 4/2011 | Jimenez | A46B 15/0097 15/22.1 |
| 8,137,109 B2 | 3/2012 | Gatzemeyer et al. | |
| 8,224,024 B2 | 7/2012 | Foxlin et al. | |
| 8,272,091 B2 | 9/2012 | Hwang et al. | |
| 8,726,915 B1 | 5/2014 | Wilkinson | |
| 9,427,078 B2 | 8/2016 | Farrell et al. | |
| 9,642,684 B2 | 5/2017 | Yoshida et al. | |
| 9,750,586 B2 | 9/2017 | Hwang et al. | |
| 2004/0187889 A1* | 9/2004 | Kemp | A46B 15/0097 15/176.1 |
| 2009/0092955 A1 | 4/2009 | Hwang | |
| 2009/0215015 A1 | 8/2009 | Chu | |
| 2014/0065588 A1 | 3/2014 | Jacobson et al. | |
| 2015/0044629 A1 | 2/2015 | Wang et al. | |
| 2015/0127371 A1 | 5/2015 | Dykes et al. | |
| 2015/0335145 A1 | 11/2015 | Bloch et al. | |
| 2016/0022024 A1 | 1/2016 | Vetter et al. | |
| 2016/0022398 A1 | 1/2016 | Vetter et al. | |
| 2016/0081778 A1 | 3/2016 | Hwang et al. | |
| 2017/0065386 A1 | 3/2017 | Farrell et al. | |
| 2017/0116665 A1 | 4/2017 | Alzahrani | |
| 2017/0238692 A1* | 8/2017 | Sarubbo | G06Q 10/06398 |
| 2017/0318954 A1 | 11/2017 | Nishiura et al. | |
| 2020/0037748 A1 | 2/2020 | Gatzemeyer et al. | |
| 2021/0120947 A1 | 4/2021 | Machiorlette et al. | |

FOREIGN PATENT DOCUMENTS

| | | |
|---|---|---|
| CN | 106998900 | 8/2017 |
| KR | 101568105 | 6/2015 |
| KR | 20150063322 | 6/2015 |
| RU | 244593801 | 3/2012 |
| WO | 2010/134049 | 11/2010 |
| WO | 2014/036423 | 3/2014 |
| WO | 2014/202250 | 12/2014 |
| WO | 2016/047793 | 3/2016 |
| WO | 2017/001399 | 1/2017 |
| WO | 2017/029469 | 2/2017 |
| WO | 2018/046723 | 3/2018 |

* cited by examiner

POWERED ORAL CARE IMPLEMENT INCLUDING A TRACKING MODULE AND TRACKING MODULE THEREOF

CROSS-REFERENCE TO RELATED APPLICATIONS

The present application is a divisional of U.S. patent application Ser. No. 16/053,840, filed Aug. 3, 2018, now U.S. Pat. No. 11,297,933, the entirety of which is incorporated herein by reference.

BACKGROUND

There is a current trend where people desire to have more data about their daily habits readily presented to them. For example, many people use watches and smart phones to track their daily movements including counting their steps, distance walked, calories burned, and the like. However, people's desire for information is not limited to exercise and movement, but expands into all categories of life, including oral care. One reason that there is a desire to obtain information about a user's oral hygiene habits is to assist parents in ensuring that their children are properly brushing their teeth. In this regard, expensive electronic-based oral care implements have been developed that track this information. However, there continues to be a need to improve these devices, both aesthetically and functionally, and in terms of price-point. Thus, a need exists for an improved oral care implement with tracking functionality.

BRIEF SUMMARY

In one aspect, the invention may be a powered oral care implement comprising: an upper outer casing comprising an upper cavity having an open bottom end, the upper outer casing defining an upper gripping portion of the powered oral care implement; an electronics assembly mounted to the upper outer casing and at least partially positioned within the upper cavity; a tracking module comprising: a lower outer casing detachably coupled to the upper outer casing to enclose the open bottom end of the upper cavity and define a lower gripping portion of the powered oral care implement; and a tracking unit integrated into the lower outer casing and configured to facilitate tracking at least one of a position, orientation, or movement of the powered oral care implement within an oral cavity of a user.

In another aspect, the invention may be a tracking module of a powered oral care implement, the tracking module comprising: a lower outer casing extending from a bottom end to a top end along a longitudinal axis, the lower outer casing having an inner surface that defines a cavity having an open top end, the lower outer casing comprising a connection element that is configured to mate with a connection element on an upper outer casing of the powered oral care implement to couple the lower outer casing to the upper outer casing; and a tracking unit integrated into the lower outer casing and configured to facilitate tracking at least one of a position, orientation, or movement of the oral care implement.

In yet another aspect, the invention may be a powered oral care implement having an interchangeable gripping portion, the powered oral care implement comprising: an upper outer casing comprising an upper cavity having an open bottom end, the upper outer casing defining an upper gripping portion of the powered oral care implement; an electronics assembly mounted to the upper outer casing and positioned within the upper cavity; a first lower outer casing; a tracking module comprising: a second lower outer casing; and a tracking unit integrated into the second lower outer casing and configured to facilitate tracking at least one of a position, orientation, or movement of the powered oral care implement within an oral cavity of a user; and wherein the first and second lower outer casings can be interchangeably detachably coupled to the upper outer casing to enclose the open bottom end of the upper cavity and define a lower gripping portion of the powered oral care implement In a further aspect, the invention may be a method of assembling a powered oral care implement, the method comprising: providing an upper outer casing of the oral care implement, the upper outer casing having an open bottom end; mounting an electronics assembly to the upper outer casing; providing a tracking module comprising a lower outer casing and a tracking unit integrated into the lower outer casing, wherein the tracking unit is configured to facilitate tracking at least one of a position, orientation, or movement of the powered oral care implement within an oral cavity of a user; coupling the lower outer casing to the upper outer casing in a detachable manner so that the lower outer casing closes the open bottom end of the upper outer casing, the upper outer casing defines an upper gripping portion of the powered oral care implement, and the lower outer casing defines a lower gripping portion of the powered oral care implement.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
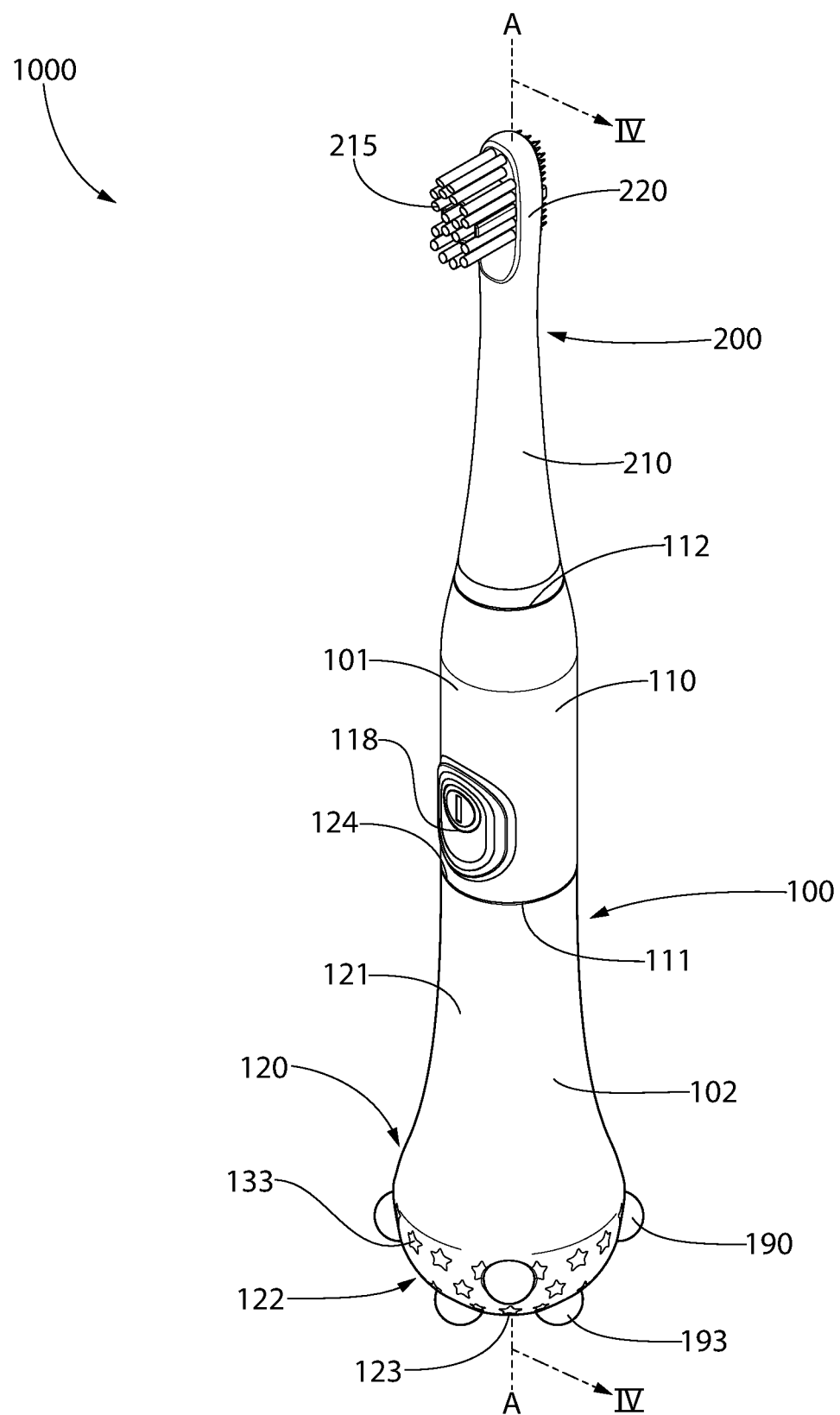
FIG. 1 is a front perspective view of a powered oral care implement in accordance with an embodiment of the present invention.
Figure 2:
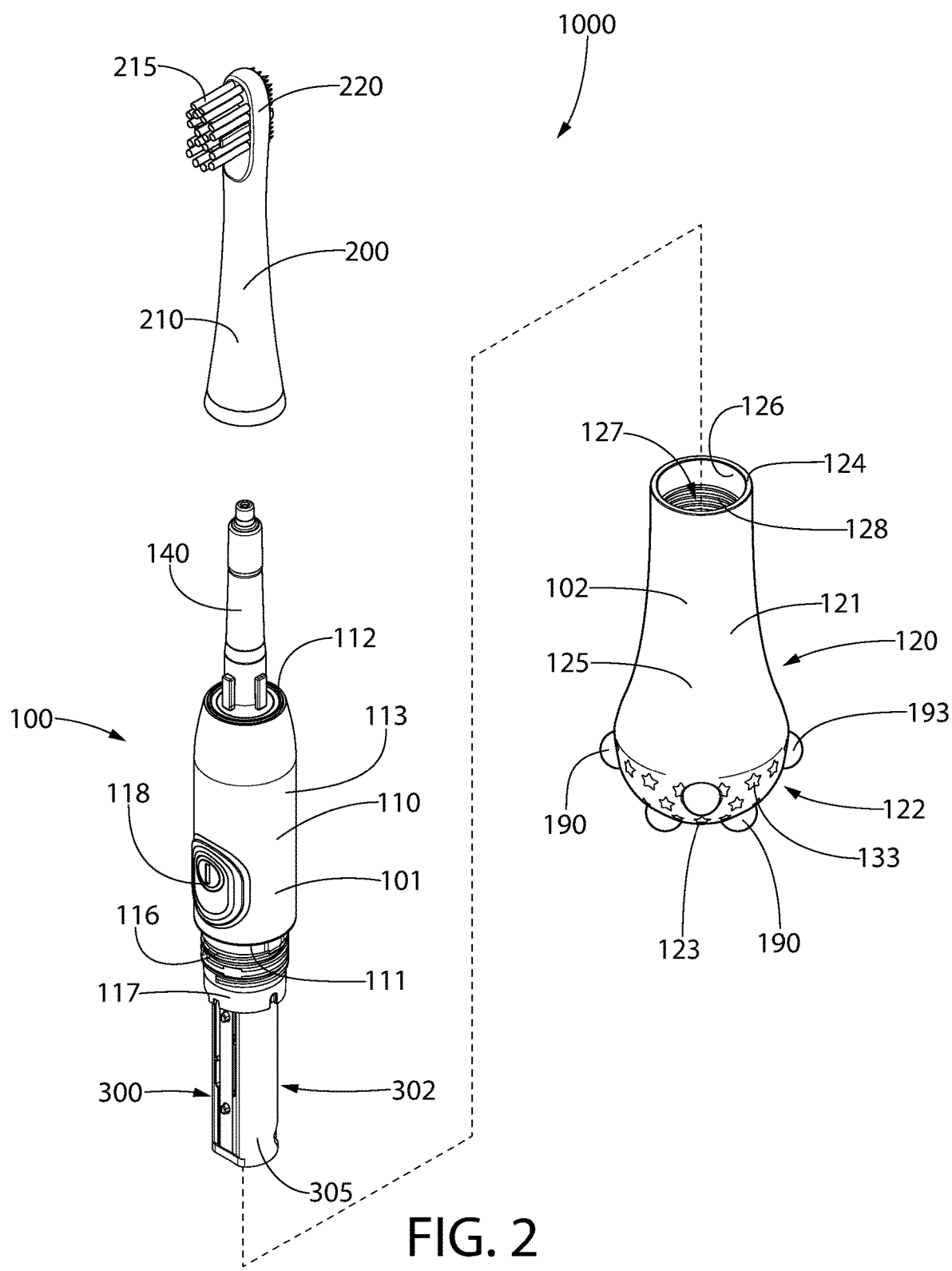
FIG. 2 is a partially exploded view of the powered oral care implement of FIG. 1.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Referring to FIGS. 1-5, a powered oral care implement 1000 will be described in accordance with an embodiment of the present invention. The powered oral care implement 1000 generally comprises a handle 100 and a replacement head 200 that is detachably coupled to the handle 100. The replacement head 200 may be repetitively coupled to and decoupled from the handle 100 as desired. This enables the handle 100 to be kept and reused while the replacement head 200 is replaced with a new replacement head 200 when the cleaning elements of the replacement head 200 become worn. Of course, the invention is not limited to the powered oral care implement 1000 having a replacement head, and in other embodiments the powered oral care implement 1000 may have a permanently affixed head.

In the exemplified embodiment, the powered oral care implement 1000 is a powered or electric toothbrush (including a vibratory element that moves a bristle holder or vibrates the head or portions thereof). Of course, the invention is not to be so limited in all embodiments and in other embodiments the disclosure set forth herein may be applicable to a manual oral care implement or toothbrush. In still other embodiments, the disclosure set forth herein may be applicable to a tongue scraper, a gum and soft tissue cleanser, a water pick, an interdental device, a tooth polisher, a specially designed ansate implement having tooth engaging elements, or any other type of implement that is commonly used for oral care.

The handle 100 extends along a longitudinal axis A-A and includes an upper outer casing 110, a tracking module 120, and a stem 140. The tracking module 120 comprises a lower outer casing 121 and a tracking unit 122, the details of which will be provided below. The lower outer casing 121 of the tracking module 120 is detachably coupled to the upper outer casing 110 such that the upper outer casing 110 forms an upper gripping portion 101 of the handle 100 and the lower outer casing 121 forms a lower gripping portion 102 of the handle 100. Thus, in some embodiments the tracking module 120, and more specifically the lower outer casing 121 thereof, forms an integral or necessary part of the handle 100. Specifically, the upper outer casing 110 may be too small to be easily gripped by a user by itself for performing oral hygiene activities and it is only when the tracking module 120 is coupled to the upper outer casing 110 that the handle 100 is sufficiently long to be readily gripped by a user. Thus, the tracking module 120 not only performs a tracking function (described in more detail below), but it also performs a handling function in that without it, a user may have great difficulty using the powered oral care implement 1000 properly (in some embodiments it may be impossible to use the powered oral care implement 1000 without the tracking module 120 attached to the upper outer casing 110. This is different than many of the tracking modules currently in existence that do not form an integral part of the toothbrush to which they are attached, but rather that receive a portion of the toothbrush within a sleeve to attach to the toothbrush. As will be discussed in more detail below, the stem 140 protrudes from a top end of the upper outer casing 110 and may include features that facilitate the coupling of the replacement head 200 to the handle 100.

The handle 100 is the portion of the powered oral care implement 1000 that is typically gripped by a user during oral hygiene activities such as toothbrushing. Thus, the handle 100 is an elongated structure that provides the mechanism by which the user can hold and manipulate the powered oral care implement 1000 during use. The portion of the handle 100 that is gripped by a user during oral hygiene activities is formed collectively by the upper outer casing 110 and the lower outer casing 121 of the tracking module 120. In the exemplified embodiment, the upper and lower outer casings 110, 121 are formed of a rigid plastic material, such as for example without limitation polymers and copolymers of ethylene, propylene, butadiene, vinyl compounds and polyesters such as polyethylene terephthalate. The handle 100 may also include resilient gripping portions overmolded onto or otherwise coupled to the rigid plastic material to enhance the gripping experience for a user, although this is not shown in the exemplified embodiment and is not required in all embodiments.

The upper outer casing 110 extends from a bottom end 111 to a top end 112 and has an outer surface 113 and an inner surface 114. The inner surface 114 of the upper outer casing 110 defines an upper cavity 115 of the upper outer casing 110. The upper cavity 115 has an open bottom end at the bottom end 111 of the upper outer casing 110 and an open top end at the top end 112 of the upper outer casing 110. Specifically, there is an opening in each of the bottom and top ends 111, 112 of the upper outer casing 110. Thus, the upper cavity 115 is open at both opposing ends of the upper outer casing 110 such that the upper cavity 115 may be more of a passageway than a cavity. In alternative embodiments, one of the top and bottom ends of the upper cavity 115 may be closed.

The upper outer casing 110 comprises a first connection element 116 that facilitates the coupling of the upper outer casing 110 to the tracking module 120. In the exemplified embodiment, the upper outer casing 110 comprises a neck portion 117 that extends from the bottom end 111 of the upper outer casing 110. Furthermore, in the exemplified embodiment the first connection element 116 is located on the neck portion 117. In the exemplified embodiment, the first connection element 116 comprises screw threads located on the neck portion 117 of the upper outer casing 110. However, the invention is not to be so limited in all embodiments and the first connection element 116 may take on other structural forms, such as being a notch, indent, detent, fastener, lock/key, or merely a shape that fits with a shape of the lower outer casing 121 in an interference or friction-type fit to couple those two casings together in a detachable manner. Thus, the specific structure of the first connection element 116 is not to be limited to that which is shown in the exemplified embodiment unless specifically claimed as such.

The upper outer casing 110 also comprises an actuator 118 that, when actuated, activates a motor to cause vibrations in the replacement head 200 (or, more specifically, to cause vibrations in the stem 140 which are then transmitted to the replacement head 200 when the replacement head 200 is coupled to the handle 100). In the exemplified embodiment, the actuator 118 is a portion of the upper outer casing 110 that is flexible or resilient so that it can be pressed inwardly towards a switch to power the motor on and off. In the exemplified embodiment, this is achieved by surrounding a portion of the upper outer casing 110 with a resilient material 119 that permits the portion of the upper outer casing 110 to be flexed radially relative to the remainder of the upper outer casing 110 such that the actuator 118 can be pressed into contact with a switch to power a motor on and off as described below.

As noted above, the tracking module 120 comprises a lower outer casing 121 and a tracking unit 122 that is integrated into the lower outer casing 121. The tracking module 120 may be configured, by itself or in conjunction with an external electronic device such as a camera, a processor, a memory device, and software and/or algorithms, to track the position, orientation, movement, location in the oral cavity, or the like of the powered oral care implement 1000 or portions thereof. In some embodiments, the invention may be directed to the tracking module 120 itself.

The tracking unit 122 of the tracking module 120 is configured to track at least one of a position, orientation, movement, location in the oral cavity, or the like of the powered oral care implement of which the tracking module 120 forms a part. In the exemplified embodiment, the tracking unit 122 comprises a plurality of visual markers that are viewed by a camera to perform the tracking function. However, the invention is not to be so limited and in other embodiments the tracking unit 122 may comprise an accelerometer, a gyroscope, sensors, or other electronic components that facilitate the position, orientation, movement, or location tracking function. In still other embodiments, the tracking unit 122 may include both visual markers as described herein as well as one or more of an accelerometer, gyroscope, or other sensors.

In the exemplified embodiment, the tracking module 120 is merely structural and does not include any electrical components. Thus, the tracking module 120 is free of a power source, battery, processor, controller, sensors, electrodes, chips, printed circuit boards, circuits, resistors, capacitors, inductors, transistors, transformers, switches, fuses, conductors, or any other type of device that may be considered an electrical component. Rather, the tracking module 120 is formed entirely of non-electrical components, and the tracking module 120 also does not house any electrical components that perform a tracking function (although some electrical components that are used to vibrate the head may be housed within the tracking module 120). Of course, alternative embodiments are possible where the tracking module 120 may include electrical components such as any of one or more of the components noted above or in particular an accelerometer, gyroscope, or the like.

The tracking module 120, and more specifically the tracking unit 122 thereof, is configured to operate to track characteristics of the powered oral care implement 1000 related to its movement. The tracking module 120 is capable of doing this despite being free of electrical components in the exemplified embodiment. When the tracking module 120 is used in conjunction with a camera and specifically formulated software and algorithms, the tracking module 120 assists in tracking the movement, position, orientation, or the like of the powered oral care implement 1000 of which it forms a part. Specifically, one or more external electronic devices that include a camera, a processor, a memory device, and the required software and algorithms can track movement of the powered oral care implement 1000 based on the location of various visual markers (described below) that form a part of the tracking unit 122 of the tracking module 120. The structural features of the tracking module 120 will be described in detail herein. However, the algorithms, software, and processors that are used to track movement of the powered oral care implement 1000 based on the visual markers of the tracking module unit 122 will not be described in any great detail herein.

The lower outer casing 121 of the tracking module 120 extends from a bottom end 123 to a top end 124 and has an outer surface 125 and an inner surface 126. The inner surface 126 of the lower outer casing 121 defines a lower cavity 127. The lower cavity 127 has a closed bottom end formed by the bottom end 123 of the lower outer casing 121 and an open top end formed by an opening that is formed into the top end 124 of the lower outer casing 121. In alternative embodiments, the lower outer casing 121 may be a solid structure rather than being hollow and comprising the lower cavity 127. Thus, in some embodiments the lower cavity 127 may be omitted.

The lower outer casing 121 comprises a second connection element 128 that facilitates the coupling of the lower outer casing 121 to the upper outer casing 110. In the exemplified embodiment, the second connection element 128 comprises screw threads that are formed along the inner surface 126 of the lower outer casing 121 adjacent to the top end 124 of the lower outer casing 121. In the exemplified embodiment, the screw threads of the second connection element 128 mate with the screw threads of the first connection element 116 to couple the upper and lower outer casings 110, 121 together. Thus, coupling of the upper and lower outer casings 110, 121 may include rotating the lower outer casing 121 relative to the upper outer casing 110 as the screw threads of the first and second connection elements 116, 128 engage one another.

Of course, the second connection element 128 may take on other structural forms, such as being a notch, indent, detent, fastener, lock/key, tabs, slots, protuberances, bayonet locking, hook-and-loop, snap-fit, magnetic engagement, or the like to couple those two casings together in a detachable manner. Thus, in some embodiments rotation of the lower outer casing 121 relative to the upper outer casing 110 may not be required to couple those two components together. In some embodiments, the first and second connection elements 116, 128 are mechanical structures so that the connection is not merely a friction fit, but it is achieved by the engagement of mechanical structures on each of the upper and lower outer casings 110, 121. In some embodiments, the second connection element 128 is a mechanical connection element that mates, interacts, or engages a connection element on the upper outer casing 110. Thus, the specific structure of the second connection element 128 is not to be limited to that which is shown in the exemplified embodiment unless specifically claimed as such. The first and second connection elements 116, 128 should be selected to ensure that they can cooperate to couple the upper and lower outer casings 110, 121 together. In some embodiments, this coupling should create a seal, and preferably a hermetic seal, as discussed further below.

Because the bottom end of the upper cavity 115 and the top end of the lower cavity 127 are open, when the upper and lower casings 110, 121 are coupled together, the upper and lower cavities 115, 127 form a single, continuous, uninterrupted volume of space (i.e., they form a singular cavity of the handle 100). Of course, in embodiments where the lower cavity 127 is omitted the upper cavity 115 forms the entirety of the singular cavity of the handle 100.

The lower outer casing 121 has a cylindrical portion 129 and a bulbous portion 130. The cylindrical portion 129 includes the top end 124 and the bulbous portion 130 includes the bottom end 123. Thus, the bulbous portion 130 of the lower outer casing 121 forms a proximal portion of the lower outer casing 121. Furthermore, the lower outer casing 121 has a flared portion 131 located between the cylindrical and bulbous portions 129, 130. Moreover, in the exemplified embodiment the transverse cross-sectional area of the lower cavity 127 decreases from the bulbous portion 130 to (or near) the top end 124 of the lower outer casing 121. Thus, the lower cavity 127 is tapered in a direction towards the top end 124 of the lower outer casing 121 in the exemplified embodiment. Of course, the exact shape of the lower outer casing 121 is not to be limited to that which is depicted in the drawings in all embodiments and it could be cylindrical along its entire length or it could include various contours, indents, detents, or the like.

In the exemplified embodiment, the tracking unit 122 comprises a plurality of visual markers 190 that are coupled to or otherwise integrated into the lower outer housing 121. In the exemplified embodiment, the plurality of visual markers 190 are coupled, attached, adhered, or affixed to the lower outer casing 121 of the tracking module 120. More specifically, in the exemplified embodiment the plurality of visual markers 190 are located along the bulbous portion 130 of the lower outer housing 121. As noted above, the lower outer casing 121 may be formed from a rigid material such as a hard plastic. Furthermore, in the exemplified embodiment, each of the plurality of visual markers 190 may be formed from a resilient material, such as silicone or a thermoplastic elastomer. In an alternative embodiment, the plurality of visual markers 190 could be formed of a rigid material such as a hard plastic. For example, in one particular embodiment the plurality of visual markers 190 could be formed from polypropylene without affecting their function.

In the exemplified embodiment, the lower outer casing 121 comprises a plurality of holes 132 that extend through the lower outer casing 121 from the outer surface 125 to the inner surface 126. Thus, each of the holes 132 forms a passageway into the lower cavity 127 from the atmosphere or external environment. The holes 132 are arranged in a spaced apart manner and they may include a first set of holes 132a that are located at or adjacent to the bottom end 123 of the lower outer casing 121 and a second set of holes 132b that are slightly elevated relative to the first set of holes 132a. In the exemplified embodiment, each of the first and second sets of holes 132a, 132b includes four separate and spaced apart holes, although more or less than four holes may be included within each set of holes 132a, 132b. The holes 132 provide a location at which the markers 190 can be coupled to the lower outer casing 121.

Each of the visual markers 190 comprises an anchor portion 191, a protruding portion 193, and an intermediate portion 192 that extends between the anchor and protruding portions 191, 193. For each of the visual markers 190, a lower surface of the anchor portion 191 forms a shoulder that extends radially at an end of the intermediate portion 192 to facilitate the coupling of the visual markers 190 to the lower outer casing 121. Specifically, the shoulder engages a portion of the lower outer casing 121 to secure the visual marker 190 to the lower outer casing 121. An upper surface of the anchor portion 191 that extends from the shoulder is chamfered to make it easier to manually couple the visual marker 190 to the lower outer casing 121. The protruding portions 193 are dome or bulbous shaped portions that protrude from the outer surface 125 of the lower outer casing 121 when the visual markers 190 are coupled thereto. In the exemplified embodiment, the protruding portions 193 are spherical or semispherical shaped. Each of the visual markers 190 located in the first set of holes 132a may have a different color from the others and similarly each of the visual markers located in the second set of holes 132b may have a different color from the others. This differentiation in the colors assists in the software reading the visual markers 190 to determine the position, orientation, and/or movement of the powered oral care implement 1000.

The visual markers 190 may be injection molded into the holes 132 or they may be formed separately from the lower outer casing 121 and manually inserted into the holes 132 to couple the visual markers 190 to the lower outer casing 121.

Although the holes 132 are depicted in the exemplified embodiment to facilitate the coupling of the visual markers 190 to the lower outer casing 121, the invention is not to be so limited in all embodiments. In alternative embodiments, the holes 132 can be replaced with basins having a floor, and the visual markers 190 may be injected into the basin cavities to couple the visual markers 190 to the lower outer casing 121. In such embodiments, the material of the visual markers 190 may chemically bond to the material of the lower outer casing 121 to facilitate the coupling therebetween. In still other embodiments, the lower outer casing 121 may have a basin (or a blind hole) with an annular channel extending from its floor so that portions of the visual marker 190 may enter into the annular channel to facilitate a proper attachment of the visual markers 190 to the lower outer casing 121. In short, the openings 132 are merely one way that the visual markers 190 may be coupled to the lower outer casing 121, but other manufacturing techniques are possible while still enabling the visual markers 190 to operate and function as the tracking unit 122 as described herein.

In the exemplified embodiment, the visual markers 190 are all located along the bulbous portion 130 of the lower outer casing 121, and the bulbous portion 130 includes the bottom end 123. Moreover, in the exemplified embodiment there is a design indicia 133 on the outer surface 124 of the lower outer casing 121 along the bulbous portion 130 thereof. Specifically, in the exemplified embodiment the design indicia 133 is a plurality of spaced apart stars. However, the invention is not to be so limited and the design indicia 133 could be any pattern of similar or different shapes, including stars, squares, triangles, irregular shapes, non-circular shapes, or the like. In some embodiments, the protruding portions 193 of the visual markers 190 are spherical or semi-spherical, thereby giving them a circular or rounded shape when viewed by a user. The design indicia 133 should include shapes or patterns that are readily distinguishable from the spherical or round shape of the protruding portions 193 of the visual markers 190. This helps the software to be drawn to the visual markers 190 to facilitate performance of the tracking function as described herein. Furthermore, the color of the design indicia 133 (i.e., the stars) may in some embodiments be different than the color of each of the visual markers 190.

Figure 4:
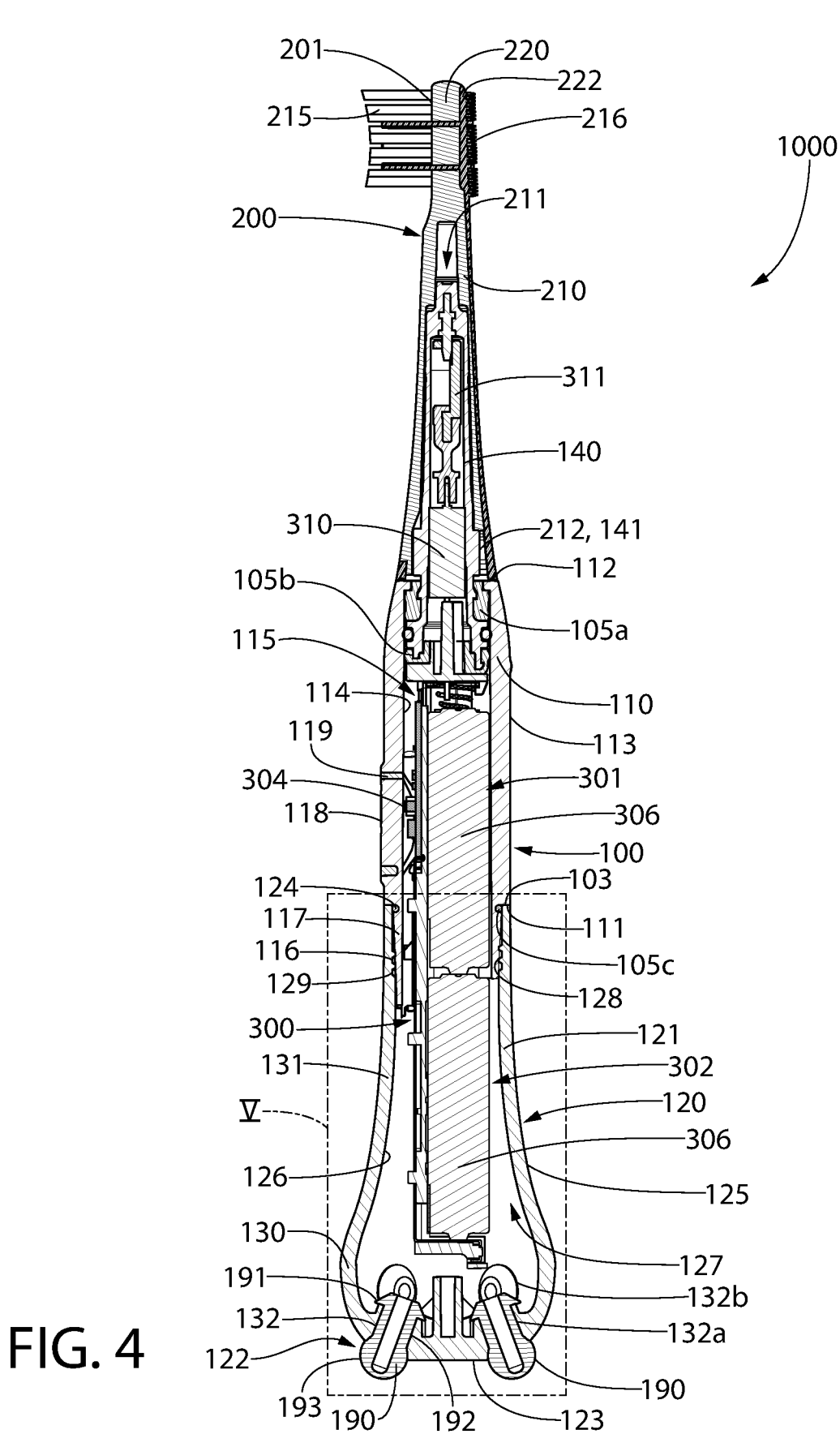
FIG. 4 is a cross-sectional view taken along line IV-IV of FIG. 1.
Figure 5:
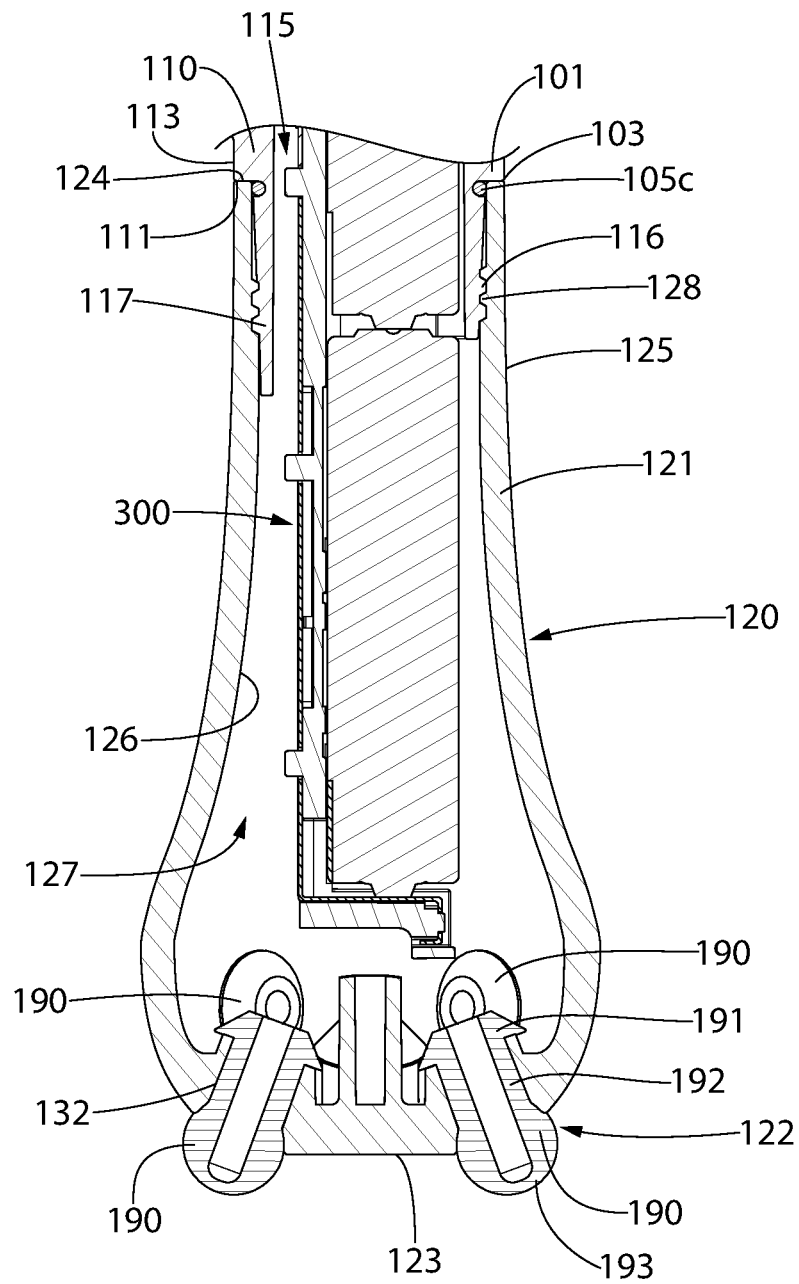
FIG. 5 is a close-up view of area V of FIG. 4.

When the upper and lower outer casings 110, 121 are coupled together as illustrated in FIGS. 1, 4, and 5, the outer surface 113 of the upper outer casing 110 and the outer surface 125 of the lower outer casing 121 are flush with one another. Stated another way, the upper outer casing 110 forms the upper gripping portion 101 of the handle 100 and the lower outer casing 121 forms the lower gripping portion 102 of the handle 100 and there is a smooth transition between the upper and lower outer casings 110, 121 at an interface 103 thereof. Furthermore, when the upper and lower outer casings 110, 121 are coupled together, the top end 124 of the lower outer casing 121 is in abutment with the bottom end 111 of the upper outer casing 110 and the neck portion 117 of the upper outer casing 110 extends into the lower cavity 127. Of course, in other embodiments the upper outer casing 110 may not include the neck portion 117.

Figure 3:
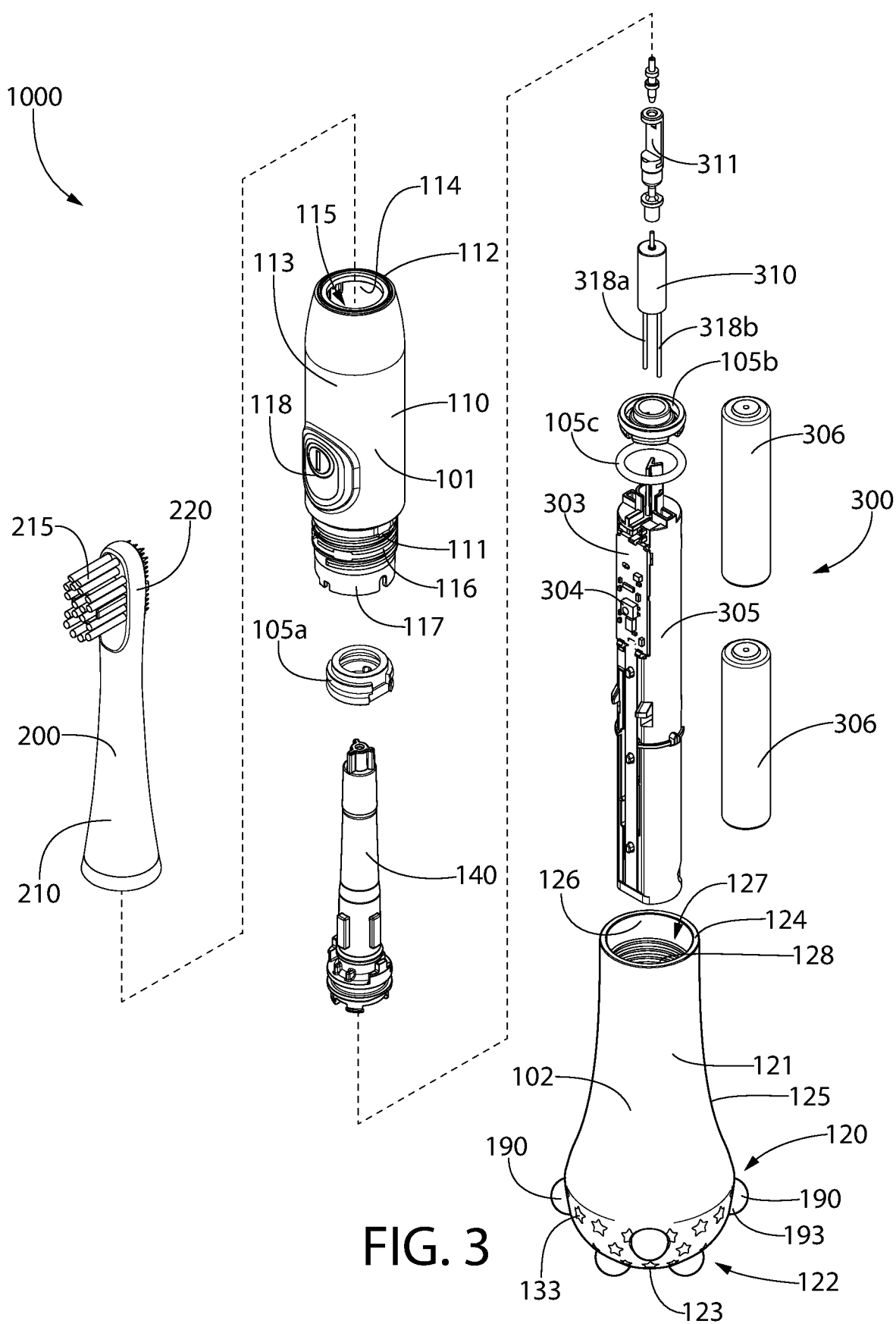
FIG. 3 is a fully exploded view of the powered oral care implement of FIG. 1.

Thus, the top end 124 of the lower outer casing 121 does not protrude radially relative to the bottom end of the upper outer casing 110 and vice versa. The coupling of the upper and lower outer casings 110, 121 forms a hermetic seal that prevents the ingress of liquid into the upper cavity 115 (and also into the lower cavity 127) at the interface 103 of the upper and lower outer casings 110, 121. Gaskets, seals, O-rings, or the like may be incorporated into or attached to one or both of the upper and lower outer casings 110, 121 along or adjacent to the interface 103 (or at least along the first and second connection elements 116, 128) to facilitate the formation of the hermetic seal. Several such gaskets, seals, and O-rings 105a-c are illustrated in FIGS. 3 and 5.

When the upper and lower outer casings 110, 121 are coupled together, an outer surface of the upper and lower gripping portions 101, 102 are flush at the interface 103 of the upper and lower outer casings 110, 121. Thus, the tracking module 120 does not form a sleeve within which the upper outer casing 110 is disposed, but rather the tracking module 120, and specifically the lower outer casing 121 thereof, together with the upper outer casing 110 form a smooth, continuous, flush, uninterrupted outer surface of the handle 100. Only the neck portion 117 of the upper outer casing 110 is disposed within the lower cavity 127 of the lower outer casing 121 when the upper and lower outer casings 110, 121 are coupled together because this is required to achieve engagement/interaction of the first and second connection elements 116, 128 in the exemplified embodiment. Otherwise, the lower cavity 127 is not intended to house any portion of the upper outer casing 110. The tracking module 120 forms a position, orientation, and/or movement tracking function and also forms a part of the gripping portion of the handle 100 that is gripped by a user during oral hygiene activities.

The upper outer casing 110 has a first length measured from the bottom end 111 to the top end 112. Furthermore, the lower outer casing 121 has a second length measured from the bottom end 123 to the top end 124. In some embodiments, the second length may be equal to or greater than the first length. In other embodiments, the second length may be greater than the first length. Thus, the lower outer casing 121 forms a longer portion (in the direction of the longitudinal axis A-A) of the gripping portion of the handle 100 than the upper outer casing 110. Of course, it is possible in alternative embodiments for the opposite to be true and for the first length of the upper outer casing 110 to be greater than the second length of the lower outer casing 121.

As mentioned above, the handle 100 also comprises a stem 140 that protrudes from the top end 112 of the upper outer casing 110. The stem 140 is not directly attached to the upper outer casing 110 in the exemplified embodiment, but rather it extends through the open top end of the upper outer casing 110. Thus, stating that the stem 140 protrudes from the top end 112 of the upper outer casing 110 does not require a direct coupling between the stem 140 and the top end 112 of the upper outer casing 110, but merely requires that the stem 140 extends in the direction of the longitudinal axis A-A beyond the top end 112 of the upper outer casing 110. Of course, the stem 140 may be directly coupled to the upper outer casing 110 in other embodiments. The stem 140 houses some components of an electronics assembly of the powered oral care implement 1000 (described below) and also serves as the attachment point for the replacement head 200.

The replacement head 200 comprises a sleeve portion 210 having a cavity 211 and a head portion 220. The sleeve portion 210 fits over the stem 140 of the handle 100 to couple the replacement head 200 to the handle 100. Thus, the stem 140 is positioned within the cavity 211 of the sleeve portion 210 when the replacement head 200 is coupled to the handle 100. In some embodiments, the sleeve portion 210 and the stem 140 may have mating or engaging locking features that facilitate the coupling of the replacement head 200 to the handle 100. Specifically, the sleeve portion 210 may include a locking aperture 212 that mates with a locking protuberance 141 located on the stem 140 or vice versa (i.e., the locking protuberance may be located on the sleeve portion 210 and the locking aperture may be located on the stem 140). The head portion 220 of the replacement head 200 has a front surface 221 with a plurality of tooth cleaning elements 215 extending therefrom for cleaning a user's oral cavity such as the teeth and gums. The replacement head 200 may also have a rear surface 222 with a tongue cleaner 216 thereon.

The exact structure, pattern, orientation and material of the tooth cleaning elements 215 is not to be limiting of the present invention unless so specified in the claims. Thus, as used herein the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, multi-component bristles including spiral bristles and core-sheath bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 215 of the present invention can be connected to the head portion 220 in any manner known in the art. For example, staples/anchors, in-mold tufting (IMT) or anchor free tufting (AFT) could be used to mount the cleaning elements/tooth engaging elements. In certain embodiments, the invention can be practiced with various combinations of stapled, IMT or AFT bristles. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

The powered oral care implement 1000 also comprises an electronics assembly 300 that is housed partially within the stem 140, partially within the upper cavity 115, and partially within the lower cavity 127. In certain embodiments, the electronics assembly 300 is mounted to the upper outer casing 110 and at least partially positioned in the upper cavity 115 of the upper outer casing 110. More specifically, when the electronics assembly 300 is mounted to the upper outer casing 110, a first portion 301 of the electronics assembly 300 is located within the upper cavity 115 and a second portion 302 of the electronics assembly 300 protrudes from the open bottom end of the upper cavity 115 (see FIG. 2). When the lower outer casing 121 is coupled to the upper outer casing 110, the second portion 302 of the electronics assembly 300 is positioned within the lower cavity 127. Of course, the invention is not to be limited in this regard and in alternative embodiments the entirety of the electronics assembly 300 may be located within the upper cavity 115 and a cavity defined by the stem 140 such that no part of the electronics assembly 300 protrudes from the bottom end 111 of the upper outer casing 110. This may be required in embodiments whereby the tracking module 120, and more specifically the lower outer casing 121 thereof, is solid rather than hollow.

In the exemplified embodiment, the electronics assembly 300 comprises a circuit board 303 comprising the electronic circuitry necessary for proper operation of the powered oral care implement 1000, including processor(s), memory device(s), switch(es) (such as switch 304), resistors, capacitors, conductors, wires, support structures, fasteners, and the like. The electronics assembly 300 also comprises a chassis 305 that holds a power source 306, which is shown as two batteries exploded away from the electronics assembly 300 in FIG. 3. Of course, more or less than two batteries may be used depending on need and size constraints. In the exemplified embodiment, the circuit board 303 is coupled to one side of the chassis 305 and the batteries 306 are housed within a compartment located on the opposite side of the chassis 305. Of course, other arrangements are possible in other embodiments. In some embodiments, the electronics assembly 300 may include one or more of any combination of the elements or components noted above. In some embodiments the electronics assembly 300 may consist only of the power source 306. In some embodiments, the electronics assembly 300 may also include lights, components that generate sound, or the like. The electronics assembly 300 may in some embodiments include any features that render the powered oral care implement 1000 a smart or interactive toothbrush with electronic capabilities.

The electronics assembly 300 also comprises a motor 310 that is operably coupled to the power source 306 via conductive members (i.e., wires 318a, 318b) and a vibratory element 311 that is operably coupled to the motor 310. When the switch 304 is closed, power is transmitted from the power source 306 to the motor 310 and when the switch is open power is unable to be transmitted from the power source 306 to the motor 310. Actuation of the actuator 118 controls the opening and closing of the switch 304. Specifically, pressing the actuator 118 once will alter the switch 304 from the open state to the closed state and operating the actuator 118 a second time will alter the switch 304 from the closed state to the open state.

When fully assembled, at least a portion of the power source 306 is located within the lower cavity 127 of the lower outer casing 121 and another portion of the power source 306 is located within the upper cavity 115 of the upper outer casing 210. Furthermore, at least a portion of the motor 310 and the vibratory element 311 are located within the cavity 211 of the sleeve 210 of the replacement head 200. When the switch 304 is closed, power is transmitted to the motor 310 which causes the motor 310 to rotate. Furthermore, due to its operable coupling to the motor 310, rotation of the motor 310 is imparted to the vibratory element 311 and thus when the switch 304 is closed the vibratory element 311 is also rotating. In some embodiments, the vibratory element 311 may be an eccentric having an offset portion or an offset weight distribution. Due to the offset portion of the eccentric, rotation of the vibratory element 311 creates vibrations within the stem 140 that are transmitted to the replacement head 200 when the stem 140 is located within the cavity 211 of the sleeve 210 of the replacement head 200. Of course, the vibratory element 311 is not limited to being an eccentric and in other embodiments the vibratory element 311 could be piezoelectric elements or the like. When powered on, the motor 310 and vibratory element 311 generate vibrations that are transmitted to the replacement head 200 and specifically the tooth cleaning elements 215 thereof to assist in the tooth and gum cleaning process.

In the embodiment described herein, the tracking module 120 forms a part of the powered oral care implement 1000, and more specifically the handle 100 thereof. Furthermore, the tracking module 120 can be used in conjunction with specifically formulated software and algorithms, to facilitate or otherwise assist in tracking the movement, position, orientation, location in the oral cavity (i.e., upper left quadrant, upper right quadrant, lower left quadrant, lower right quadrant, etc.) or the like of the powered oral care implement 1000. In some embodiments, the tracking module 120 may track the movement, position, orientation, location, or the like of the head portion 220 (or the tooth cleaning elements 215) of the replacement head 200.

Specifically, during use a camera is positioned so that the tracking module 120, and more specifically the tracking unit 122 thereof (which, in the exemplified embodiment, are the visual markers 190), is in the field of view of the camera. The algorithms associated with an external electronic device may be able to track the movement, position, orientation, location in the oral cavity, or the like of the powered oral care implement 1000 based on the colors of the visual markers 190 that the camera perceives. Thus, the tracking module 120 forms an integral part of the powered oral care implement 1000 and works in tandem with a camera, processor, memory, software, and/or algorithms to track the motion, movement, position, location, orientation, or the like of the powered oral care implement 1000 during a toothbrushing or oral care session. Although the tracking element module 120 does not include any electronics or sensors such as accelerometer or gyroscopes in the exemplified embodiment, it could include such components in other embodiments to aid in tracking motion of the powered oral care implement 1000.

Figure 6:
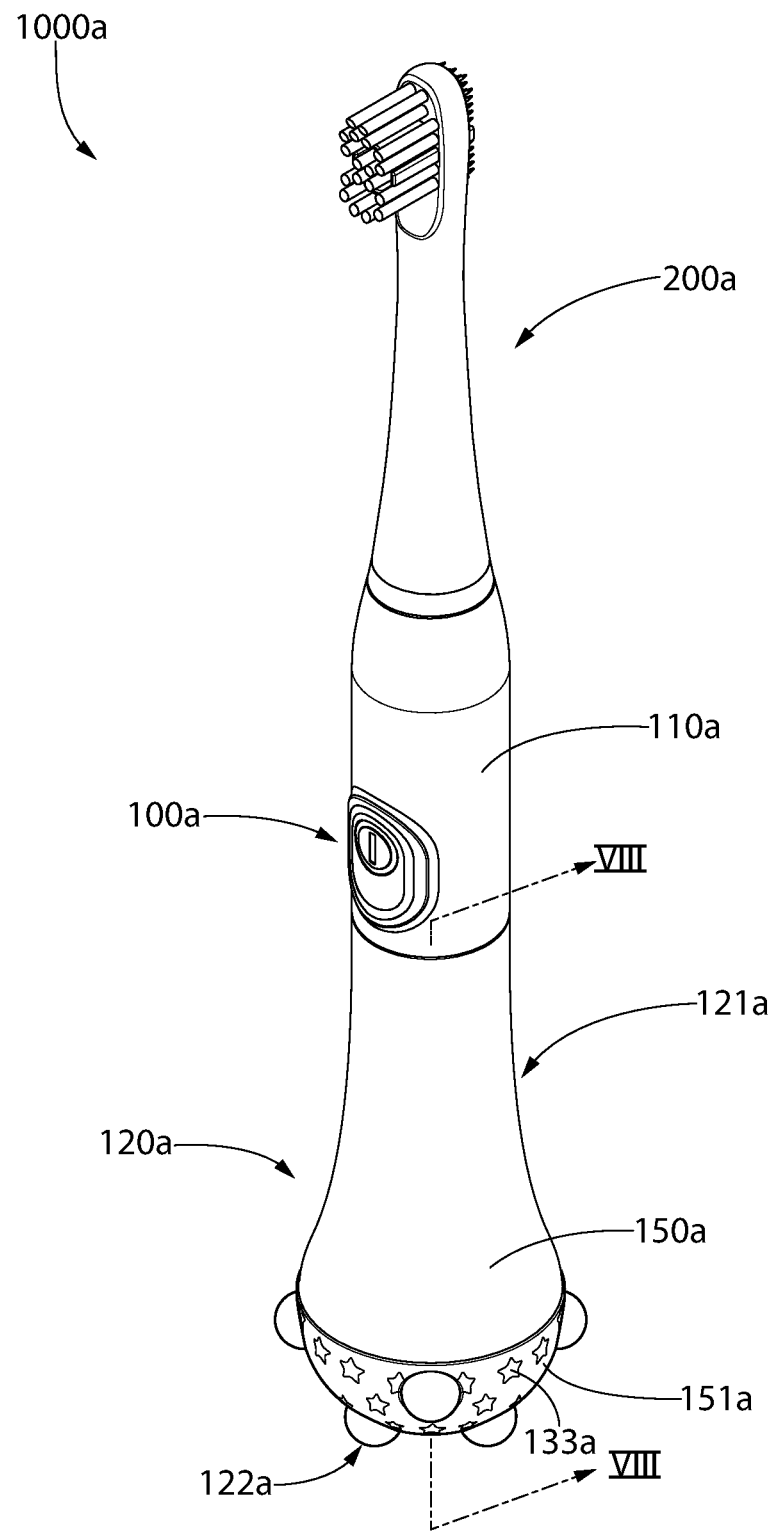
FIG. 6 is a front perspective view of a powered oral care implement in accordance with another embodiment of the present invention.
Figure 7:
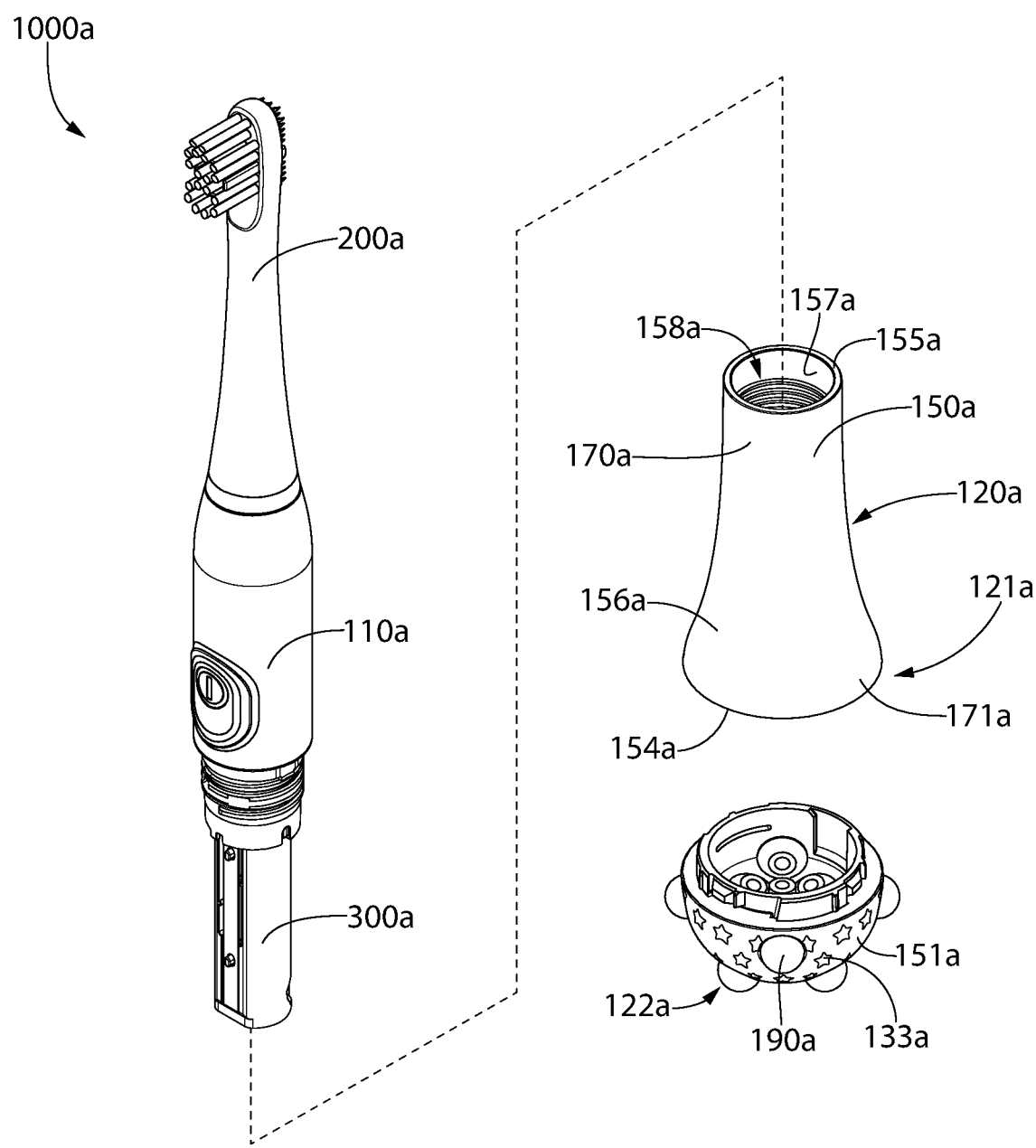
FIG. 7 is a partially exploded view of the powered oral care implement of FIG. 6.
Figure 8:
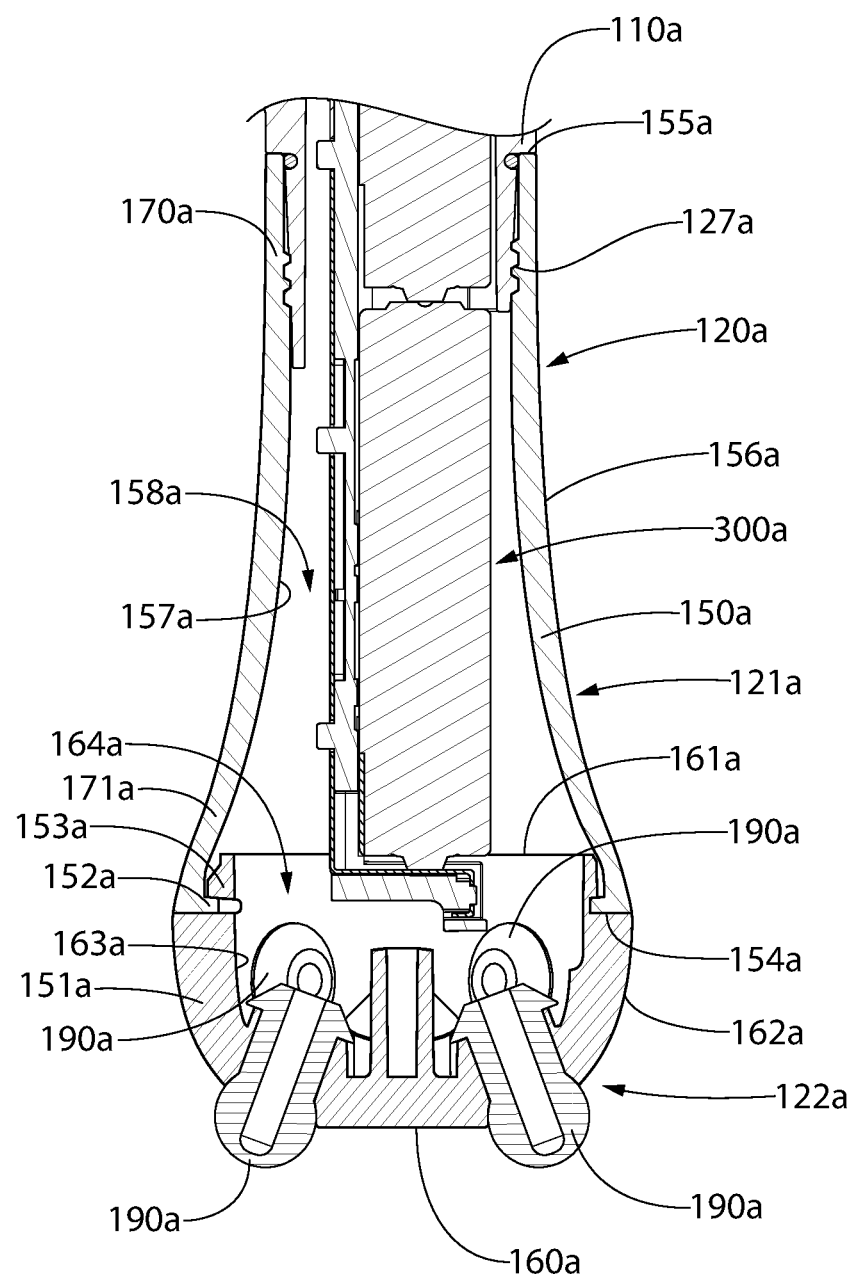
FIG. 8 is a cross-sectional view taken along line VIII-VIII of FIG. 8.

FIGS. 6-8 illustrate an alternative embodiment of a powered oral care implement 1000a in accordance with an embodiment of the present invention. Some features of the oral care implement 1000a that are similar to features of the oral care implement 1000 described above will be similarly numbered except that the suffix "a" will be added after the number to distinguish between the embodiments. Some features will be numbered but not described, it being understood that the description of the similarly numbered feature of the oral care implement 1000 is applicable. Moreover, some features and components of the oral care implement 1000a will not be described or denoted with a numeral herein, it being understood that the description of the similar feature of the oral care implement 1000 is applicable.

The powered oral care implement 1000a is identical to the powered oral care implement 1000 except that the lower outer casing 121a is formed from two parts rather than a single part as with the lower outer casing 121. Specifically, the lower outer casing 121a comprises a first part 150a and a second part 151a that are detachably coupled together. To facilitate such coupling, each of the first and second parts 150a, 151a may include connection features such as mating screw threads, tabs, indents and detents, keys and keyholes, protrusions and notches, shapes and/or sizes that create a friction or interference fit, or the like. In the exemplified embodiment, the connection features include a tab or flange 152a of the first part 150a and a tab or flange or opening 153a of the second part that cooperate to facilitate the coupling of the first and second parts 150a, 151a to one another (best seen in FIG. 8).

The first part 150a of the lower outer casing 121a extends from a first end 154a to a second end 155a. The first part 150a has an outer surface 156a and inner surface 157a that defines a first lower cavity 158a. The first lower cavity 158a has a first open end formed by an opening in the first end 154a of the first part 150a and a second open end formed by an opening in the second end 155a of the first part 150a. Thus, the first lower cavity 158a is open at both ends of the first part 150a of the lower outer casing 121a. The connection elements (i.e., screw threads) 127a that facilitate the coupling of the lower outer casing 121a to the upper outer casing 110a are located along the inner surface 157a of the first part 150a of the lower outer casing 121a.

In this embodiment, the tracking unit 122a is integrated into the second part 151a of the lower outer casing 121a. The second part 151a of the lower outer casing 121a extends from a first end 160a to a second end 161a and has an outer surface 162a and an inner surface 163a, the inner surface 163a defining a second lower cavity 164a. The second lower cavity 164a is open at the second end 161a of the second part 151a and closed at the first end 160a of the second part 151a. When the first and second parts 150a, 151a are coupled together, the first and second lower cavities 158a, 164a form a single, uninterrupted volume of space. Furthermore, the outer surfaces 156a, 162a of the first and second parts 150a, 151a are flush with one another even at the interface of the first and second parts 150a, 151a.

Of course, similar to the discussion below, in some embodiments the first and second lower cavities 158a, 164a may be omitted particularly where the lower outer casing 121a is not being used to house anything. In some embodiments, the first lower cavity 158a may be kept and the second lower cavity 164a may be omitted. However, in certain exemplified embodiments the lower outer casing 121a does house parts of the electronics assembly 300a and thus some sort of cavity is needed.

In this embodiment, the first part 150a of the lower outer casing 121a comprises a cylindrical portion 170a and a flared portion 171a and the second part 151a of the lower outer casing 121a comprises a semispherical shape. The cylindrical portion 170a may define a cavity having a constant transverse cross-sectional area or one that slightly increases moving from the second end 155a towards the flared portion 171a. Furthermore, the outer surface 162a of the second part 151a may include the design indicia 133a (i.e., star pattern or the like). Furthermore, the tracking unit 122a comprises the plurality of visual markers 190a including portions that protrude from the outer surface 162a of the second part 151a. The details of the design indicia 133a and the visual markers 190a are the same as that which has been described above and thus these details will not be described herein again in the interest of brevity.

Thus, the only real difference between the powered oral care implement 1000a and the powered oral care implement 1000 is that the tracking module 120a, and more specifically the lower outer housing 121a thereof, is formed from two parts that are detachably coupled together rather than being formed from a single unitary structure. However, when the first and second parts 150a, 151a are coupled together, the structure, shape, and functionality of the tracking module 120a and the lower outer housing 121a thereof is identical to the structure of the tracking module 120 and the lower outer housing 120 described above.

In some embodiments, the invention is the tracking module 120, 120a by itself without it being connected to the rest of the powered oral care implement 1000. Thus, the invention may be directed to a tracking module for a powered oral care implement 1000. The reason for this is that in some embodiments a powered oral care implement may be sold without the tracking module 120, but in its place there will be a different lower outer casing that does not include the tracking functionality that is included with the tracking module 120. Thus, the tracking module 120 may be sold separately from this powered oral care implement so that an end-user can replace the standard lower outer housing with the tracking module 120 to convert the powered oral care implement from a standard, non-tracking powered oral care implement into the powered oral care implement 1000 having tracking capabilities. In still other embodiments, the powered oral care implement 1000 may be sold as a kit with both the non-tracking lower outer casing and the tracking module.

Figure 9:
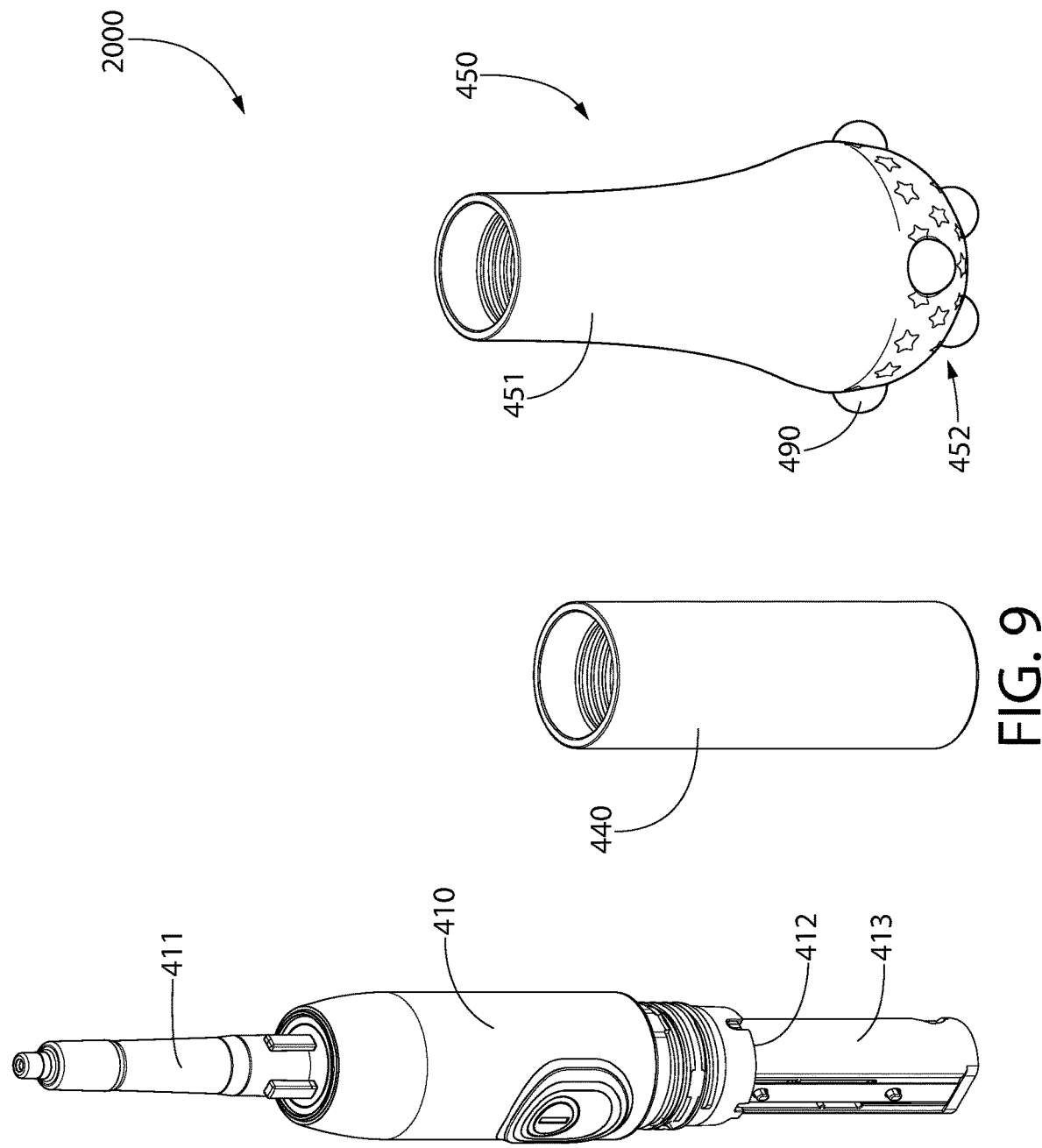
FIG. 9 illustrates a powered oral care implement kit in accordance with an embodiment of the present invention.

For example, FIG. 9 illustrates one possible embodiment of a powered oral care implement system 2000 having an interchangeable gripping portion. The powered oral care implement system 2000 comprises an upper outer casing 410 comprising an upper cavity (not visible, but the upper outer casing 410 is identical to the upper outer casing 110 described above) having an open bottom end 412. The upper outer casing 410 defines an upper gripping portion of the powered oral care implement 2000. An electronics assembly 413 is mounted to the upper outer casing 410 and protrudes from the open bottom end 412 of the upper cavity. Furthermore, a stem 411 is mounted to the upper outer casing 410 and protrudes from the top end of the upper outer casing 410.

In this embodiment, there is included a first lower outer casing 440 and a tracking module 450. The tracking module 450 comprises a second lower outer casing 451 and a tracking unit 452 integrated into the second lower outer casing 451. The tracking unit 452 is configured to facilitate the tracking of at least one of a position, orientation, or movement of the powered oral care implement system 2000. The first lower outer casing 440 and the second lower outer casing 451 can be interchangeably detachably coupled to the upper outer casing 410 to enclose the open bottom end 412 of the upper cavity of the upper outer casing 410. Whichever one of the first lower outer casing 440 and the second lower outer casing 451 is coupled to the upper outer casing 410 thereby defines a lower gripping portion of the powered oral care implement system 2000. When the first lower outer casing 440 is coupled to the upper outer casing 410, the powered oral care implement system 2000 does not include any tracking functionality. When the second lower outer casing 451 (and hence also the tracking module 450) is coupled to the upper outer casing 410, the powered oral care implement system 2000 has tracking functionalities as described herein.

In the exemplified embodiment, the first lower outer casing 440 is cylindrical and has a constant diameter and the second lower outer casing 451 has a cylindrical portion and a bulbous portion as previously described. However, in other embodiments the first and second lower outer casings 440, 451 may be identical except that the second lower outer casing 451 may have the tracking unit 452 integrated thereon. The tracking unit 452 may comprise a plurality of visual markers 490 as has been previously described in the earlier described embodiments.

The components illustrated in FIG. 9 may be sold together as a kit along with a replacement head. Alternatively, the components illustrated in FIG. 9 may be sold together as a kit without a replacement head being included in the kit. In such embodiments, the components illustrated in FIG. 9 may be packaged together. In other embodiments, the tracking module 450 may be sold separately from the upper outer casing 410, electronics assembly 413, stem 411, and first lower outer casing 440. As noted above, the tracking module 450 may be inventive in and of itself.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A tracking module of a powered oral care implement, the tracking module comprising:
a lower outer casing extending from a bottom end to a top end along a longitudinal axis, the lower outer casing having an inner surface that defines a cavity having an open top end and a connection element that is configured to mate with a connection element on an upper outer casing of the powered oral care implement to couple the lower outer casing to the upper outer casing; and
a tracking unit integrated into the lower outer casing and configured to facilitate tracking at least one of a position, orientation, or movement of the powered oral care implement;
wherein the lower outer casing comprises a first part and a second part that are detachably coupled together, and wherein the tracking unit is integrated into the second part of the lower outer casing; and
wherein the second part of the lower outer casing comprises an outer surface having a pattern of non-circular shapes thereon, and wherein the tracking unit comprises a plurality of visual markers having a spherical or semispherical portion protruding from the outer surface of the second part of the lower outer casing.

2. The tracking module according to claim 1 wherein the lower outer casing comprises a cylindrical portion that includes the top end and a bulbous portion that includes the bottom end.

3. The tracking module according to claim 1 wherein at least a portion of the cavity of the lower outer casing has a transverse cross-sectional area that decreases in a direction towards the open top end of the cavity.

4. The tracking module according to claim 1 wherein the tracking unit comprises a plurality of visual markers protruding from an outer surface of the lower outer casing.

5. The tracking module according to claim 4 wherein the lower outer casing is formed from a rigid material and each of the plurality of visual markers is formed from a resilient material.

6. The tracking module according to claim 4 wherein the lower outer casing comprises a plurality of holes extending therethrough, and wherein each of the plurality of visual markers is coupled to the lower outer casing within one of the plurality of holes, and wherein a portion of the plurality of visual markers that protrudes from the outer surface of the lower outer casing has a spherical or semispherical shape.

7. The tracking module according to claim 1 wherein the first part of the lower outer casing comprises a cylindrical portion and a flared portion and the second part of the lower outer casing has a semispherical shape.

8. The tracking module according to claim 1 wherein the lower outer casing is formed from a rigid material.

9. The tracking module according to claim 1 wherein the connection elements of the upper and lower outer casings comprise screw threads.

10. A tracking module for an oral care implement, the tracking module comprising:
an outer casing extending from a bottom end to a top end along a longitudinal axis, the outer casing having an inner surface that defines a cavity having an open top end, the inner surface comprising a threaded portion adjacent to the open top end for facilitating coupling of the tracking module to the oral care implement; and
a tracking unit comprising a plurality of visual markers that are coupled to the outer casing such that a portion of each of the plurality of visual markers protrudes from an outer surface of the outer casing, wherein the tracking unit is configured to facilitate tracking at least one of a position, orientation, or movement of the oral care implement;
wherein the outer casing comprises a first part defining at least a first portion of the cavity that extends from the open top end to an open bottom end and a second part that is detachably coupled to the first part to close the open bottom end of the first portion of the cavity, and wherein the tracking unit is located on the second part of the outer casing.

* * * * *